United States Patent [19]

Naito et al.

[11] 4,241,063

[45] Dec. 23, 1980

[54] PURINE DERIVATIVES AND THEIR USE AS BRONCHODILATORS

[75] Inventors: Takayuki Naito, Kawasaki; Susumu Nakagawa, Tokyo; Tetsuro Yamasaki; Taka-aki Okita, both of Ichikawa; Haruhiro Yamashita, Tokyo, all of Japan

[73] Assignee: Bristol-Myers Company, New York, N.Y.

[21] Appl. No.: 64,240

[22] Filed: Aug. 6, 1979

[51] Int. Cl.³ .................................... C07D 473/18
[52] U.S. Cl. .................................... 424/253; 544/277
[58] Field of Search ............... 544/276, 277; 424/253

[56] References Cited

U.S. PATENT DOCUMENTS

| | | | |
|---|---|---|---|
| 3,228,937 | 1/1966 | Adcock | 260/252 |
| 3,862,189 | 1/1975 | Schwender | 260/252 |
| 3,917,837 | 11/1975 | Lin | 424/253 |
| 3,930,005 | 12/1975 | Wojnar et al. | 424/253 |

OTHER PUBLICATIONS

Marumoto et al., Chem Pharm. Bull. 23(4) 759–744 (1975).
Robins, et al., JACS 83 2574 (1961).
Schaeffer et al., JACS 81 197–201 (1959).
Kikugawa et al., Chem. Pharm. Bull. 25(7) 1811–1821 (1977).

*Primary Examiner*—Nicholas S. Rizzo
*Attorney, Agent, or Firm*—Robert H. Uloth; Robert E. Carnahan

[57] ABSTRACT

New 2-substituted-6-amino-9-tetrahydropyran-2-yl purine derivatives are disclosed. They are orally active bronchodilators with relatively little cardiovascular side effects. A representative and preferred embodiment of this invention is 2-n-propoxy-9-(tetrahydropyran-2-yl)-9H-adenine.

7 Claims, No Drawings

PURINE DERIVATIVES AND THEIR USE AS BRONCHODILATORS

BACKGROUND OF THE INVENTION

This invention broadly relates to heterocyclic carbon compounds having drug and bio-affecting properties. More particularly, the invention concerns novel purine derivatives which have non-adrenergic smooth muscle relaxant properties making them particularly valuable in overcoming acute bronchospasm and as adjuncts in symptomatic management of chronic, obstructive pulmonary diseases (e.g. asthma, bronchitis, emphysema). It is also concerned with therapeutic methods and compositions employing one or more of the instant compounds as active ingredients.

Regarding types of non-adrenergic bronchodilators, the theophylline group of xanthine derivatives are particular prominent. For instance, aminophylline, the ethylenediamine salt of theophylline, is an effective bronchodilator which may be administered parenterally, orally, or rectally and is useful in patients where direct relaxation of bronchial muscle is desired. Notwithstanding widespread use, the xanthine class of non-adrenergic bronchodilators have major disadvantages with respect to gastric irritation, cardiovascular and central nervous system side effects. Thus, there is a need for new and effective bronchodilators with increased potency and/or fewer or reduced untoward effects. Representative compounds of the instant invention have been shown by standard pharmacological tests to have superior bronchodilating activity relative to aminophylline with reduced cardiovascular and central nervous system side effects.

The basic purine nucleus contains a six-membered pyrimidine ring fused to the five-membered imidazole ring as shown in the following plane formula with the numbering system used herein noted.

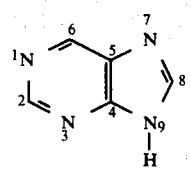

Various types of purine derivatives are known in which the parent substance purine is substituted at one or more of positions 2, 6 and 9. The following references illustrate such compounds.

1. R. K. Robins, et al., *J. Am. Chem. Soc.*, 83, 2574 (1961) describe synthesis of the compound

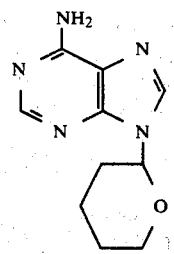

as a potential antitumor agent from 6-chloro-9-(tetrahydro-2-pyranyl)-purine.

2. U.S. Pat. No. 3,228,937 (Adcock) discloses the compound 6-benzylamino-9-tetrahydropyran-2-yl-9$\underline{H}$-purine

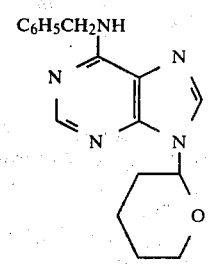

as a wilting and decay inhibitor for leafy, green plants.

3. R. Marumoto, et al., *Chem. Pharm. Bull.*, 23(4), 759–774 (1975) describes inter alia compounds of the formula

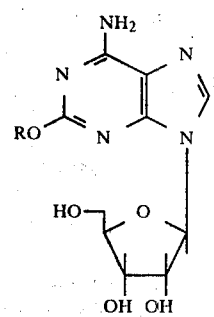

wherein R is (lower)alkyl. The compounds are said to have coronary vasodilating activity.

4. H. J. Schaeffer, et al., *J. Am. Chem. Soc.*, 81, 197–201 (1959) describes synthesis of compound having the formula

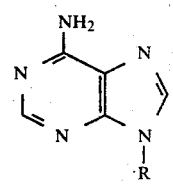

wherein R is cyclohexyl or 2-cyclohexenyl as potential anticancer agents.

5. U.S. Pat. No. 3,917,837 (Lin, et al.) discloses the use of the compound

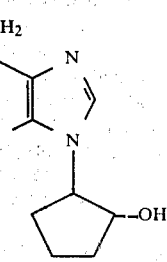

as an anti-inflammatory agent.

6. U.S. Pat. No. 3,862,189 (Schwender) concerns compounds of the formula

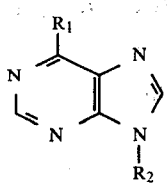

wherein, inter alia, $R_1$ is amino, alkylamino, aralkylamino, etc.; and $R_2$ is phenylalkyl, substituted phenylalkyl, tetrahydroquinoylalkyl, etc. useful as antianginal or bronchodilator agents.

7. U.S. Pat. No. 3,930,005 (Wojnar, et al.) discloses compounds of the formula

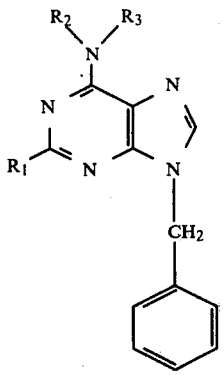

wherein $R_2$ and $R_3$ may be inter alia hydrogen and $R_1$ may be inter alia (lower)alkoxy as possessing anti-inflammatory activity.

SUMMARY AND DETAILED DESCRIPTION OF THE INVENTION

The novel purine derivatives of the instant invention are characterized by Formula I and Formula II

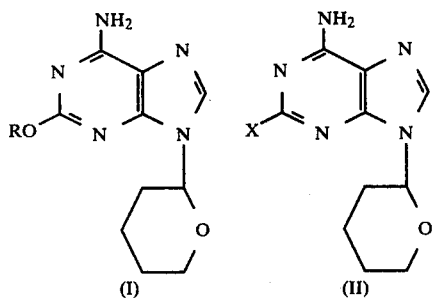

wherein R is lower alkyl of 1 to 4 carbon atoms and X is halogen or a pharmaceutically acceptable acid addition salt thereof. Said compounds effectively inhibit histamine induced bronchial constriction by acting directly on tracheal muscle to relax spasm. Thus, the compounds belong to the non-adrenergic class of bronchodilator. Formula II compounds are also useful as intermediates in the preparation of Formula I compounds, which are potent and preferred bronchodilating agents of the invention with minimal cardiovascular side effects.

It is to be understood that the term "lower alkyl" contemplates both straight and branched chain groups containing from 1 to 4 carbon atoms inclusive. Illustrative of such groups are methyl, ethyl, propyl, isopropyl, 1-butyl, 1-methylpropyl, 2-methylpropyl, and tert.-butyl. Halogen refers to chlorine, bromine, fluorine and iodine.

For the purpose of this disclosure, the term "pharmaceutically acceptable acid addition salt" denotes a salt form of a compound of Formula I or II obtained by combination with a non-toxic inorganic or organic acid which is relatively non-toxic in anionic form. Examples of non-toxic pharmaceutically acceptable acid addition salts of the compounds of Formula I or II are those formed with sulfuric, hydrochloric, phosphoric, hydrobromic, hydroiodic, sulfamic, methanesulfonic, benzenesulfonic, para-toluenesulfonic, acetic, lactic, succinic, malic, maleic, mucic, tartaric, citric, gluconic, benzoic, cinnamic, isethionic, fumaric, levulinic and related acids.

Conversion of Formula I or II compounds to corresponding non-toxic pharmaceutically acceptable acid addition salt is accomplished in conventional fashion by admixture of the base with at least one molecular equivalent of a selected acid in an inert organic solvent such as ethanol, benzene, ethylacetate, ether, halogenated hydrocarbon and the like. Isolation of the salt is carried out by techniques known to the art such as inducing precipitation with a non-polar solvent (e.g. ether) in which the salt has limited solubility.

According to the present invention, compounds of Formula I are prepared by a process comprising reacting a 2-halo-9-(tetrahydropyran-2-yl)-9H-adenine of Formula II wherein X is bromine, fluorine, iodine or preferably chlorine with an alkali metal alkoxide of the formula ROM wherein R is as defined above and M represents sodium or potassium in an inert solvent, preferably a lower alkanol ROH wherein R is as defined above, to produce the Formula I compound as the free base product. Elevated temperatures ranging from about 50° C. to 200° C. are employed in carrying out the reaction with the reflux temperature of the inert solvent preferred or in a sealed tube.

The 2-halo-9-(tetrahydropyran-2-yl)-9H-adenine intermediates of Formula II are obtained according to the following reaction scheme for the preferred compound 2-chloro-9-(tetrahydropyran-2-yl)-9H-adenine (IIa).

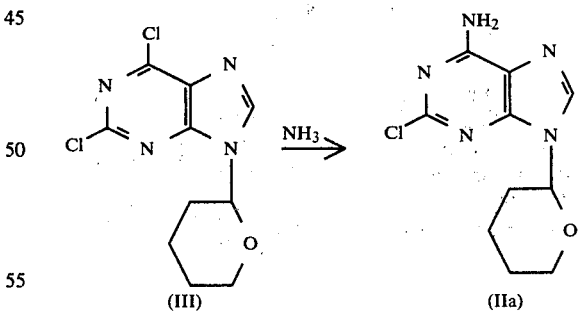

In general, the 2,6-dichloro-9-(tetrahydropyran-yl)-9H-adenine starting material (III) is suspended in an inert solvent (e.g., water, lower alkanols such as methanol, ethanol), the suspension is saturated with ammonia gas and the saturated reaction mixture heated from about 30° C. to about 150° C. in a sealed tube to complete the reaction.

According to the present invention, compounds identified by Formula I and pharmaceutically acceptable salts thereof are useful in a process for eliciting a bronchodilating effect in a mammal in need thereof which comprises systemic administration to said mammal an effective dose of from about 0.1 to 20 mg./kg. body weight of the Formula I compound. A particularly preferred compound for carrying out the process is 2-n-propoxy-9-(tetrahydropyran-2-yl)-9H-adenine. It is intended by systemic administration to include both oral and parenteral routes, e.g., intramuscular, intravenous, intraperitoneal and subcutaneous. Also, the active ingredient may be given by inhalation employing a suitable aerosol preparation. Oral administration is preferred.

Another aspect the present invention provides a pharmaceutical composition in dosage unit form useful for relief of bronchial constriction in mammals. The composition comprises, as the active ingredient, an effective bronchodilating amount of a compound of Formula I or a pharmaceutically acceptable acid addition salt thereof, in admixture with a pharmaceutically acceptable carrier or diluent.

The pharmacologically active compounds of the present invention may be administered either as individual therapeutic agents or as mixtures with other therapeutic agents. They may be administered alone, but are generally given in the form of pharmaceutical compositions. Examples of such compositions include tablets, lozenges, capsules, powders, aerosol sprays, aqueous or oily suspensions, syrups, elixirs and aqueous solutions.

The nature of the pharmaceutical composition and the pharmaceutical carrier or diluent will, of course, depend on the desired route of administration. For example, oral compositions may be in form of tablets or capsules and may contain conventional excipients such as binding agents (e.g. syrup, acacia, gelatin, sorbitol, tragacanth or polyvinylpyrrolidone), fillers (e.g. lactose, sugar, maize-starch, calcium phosphate, sorbitol or glycine), lubricants (e.g. magnesium stearate, talc, polyethylene glycol or silica), disintegrants (e.g. starch) or wetting agents (e.g. sodium lauryl sulfate). Oral liquid preparations may be in the form of aqueous or oily suspensions, solutions, emulsions, syrups, elixirs, etc. or may be presented as a dry product for reconstitution with water or other suitable vehicle before use. Such liquid preparations may contain conventional additives such as suspending agents, flavoring agents, diluents or emulsifying agents. For parenteral administration or inhalation, solutions or suspensions of a compound of Formula I with conventional pharmaceutical vehicles may be employed, e.g. as an aerosol spray for inhalation, as an aqueous solution for intravenous injection or as an oily suspension for intramuscular injection.

The compounds, pharmaceutical compositions and bronchodilating use thereof constituting embodiments of this invention are more fully illustrated by the following examples.

EXAMPLE 1

2-Chloro-9-(tetrahydropyran-2-yl)-9H-adenine

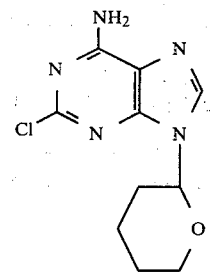

(a) 2,6-Dichloro-9-(tetrahydropyran-2-yl)-9H-purine. A solution of 2,6-dichloropurine (2.0 g., 10.6 mmoles) and 2 ml. of 3,4-dihydro-2H-pyran in 20 ml. of ethyl acetate is adjusted to pH 2 with anhydrous p-toluenesulfonic acid. The reaction mixture is warmed to 60° C. for 1 hr., neutralized with concentrated ammonium hydroxide, washed with water, dried over $Na_2SO_4$ and evaporated in vacuo. Crystallization of residual material from ethyl acetate-n-hexane affords 2.6 g. (96%) of 2,6-dichloro-9-(tetrahydropyran-2-yl)-9H-purine, m.p. 119–121° C. IR(KBr): 3100, 1600, 1560 $cm^{-1}$. UV: $\lambda_{max}^{MeOH}$ 273 nm (ε9900). NMR ($CDCl_3$): δ1.6–2.4 (6H,m), 3.5–4.4 (2H,m), 5.6–5.9 (1H,m), 8.28 (1H,s).

Anal. Calcd. for $C_{10}H_{10}Cl_2N_4O$: C, 43.98; H, 3.69; N, 20.51; Cl, 25.96. Found: C, 44.12; H, 3.45; N, 20.57; Cl, 25.44.

(b) 2-Chloro-9-(tetrahydropyran-2-yl)-9H-adenine. A suspension of 2,6-dichloro-9-(tetrahydropyran-2-yl)-9H-purine (2.0 g., 7.3 mmoles) in 50 ml. of methanol is saturated with ammonia at 0° C. during which time a solution forms. The solution is heated at 100° C. for 4 hr. in a sealed tube and cooled. Concentration of the cooled reaction mixture affords 1.55 g. (84%) of 2-chloro-9-(tetrahydropyran-2-yl)-9H-adenine, m.p. 204°–210° C. (dec.). IR(KBr): 3350, 3180, 1670, 1605 $cm^{-1}$. UV: $\lambda_{max}^{MeOH}$ 263 nm (ε14300). NMR (DMSO-$d_6$): δ1.4–2.2 (6H,m), 3.5–4.2 (2H,m), 5.13 (1H,dd, J=11 & 3 Hz), 7.73 (2H,br,s), 8.28 (1H,s).

Anal. Calcd for $C_{10}H_{12}ClN_5O$: C, 47.34; H, 4.77; N, 27.61; Cl, 13.97. Found: C, 46.84; H, 4.71; N, 27.17; Cl, 14.10.

EXAMPLE 2

2-Methoxy-9-(tetrahydropyran-2-yl)-9H-adenine

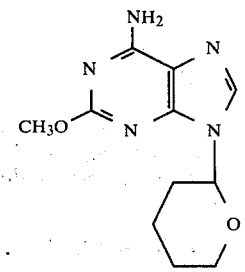

A solution of 2-chloro-9-(tetrahydropyran-2-yl)-9H-adenine (253 mg., 1 mmole) in 10 ml. of 1 N sodium methoxide in methanol heated in a sealed tube at 100° C. for a 16 hr. period, cooled and filtered affords 154 mg. of product. A second crop (49 mg.) obtained from the filtrate provides a total yield of 203 mg. (87%) of 2-methoxy-9-(tetrahydropyran-2-yl)-9H-adenine, m.p. 199° C. (dec.). IR(KBr): 3300, 1640, 1600 cm$^{-1}$. UV: $\lambda_{max}^{MeOH}$ 267 nm($\epsilon$12,100). NMR(DMSO-d$_6$): $\delta$1.4–2.2 (6H,m), 3.80 (3H,s), 3.2–4.2(2H,m), 4.47(1H,dd,J=12 & 3 Hz), 8.04(1H,s).

Anal. Calcd. for $C_{11}H_{15}N_5O_2$: C, 53.00; H, 6.07; N, 28.10. Found: C, 52.73; H, 6.13; N, 28.50.

EXAMPLE 3

2-n-Propoxy-9-(tetrahydropyran-2-yl)-9H-adenine

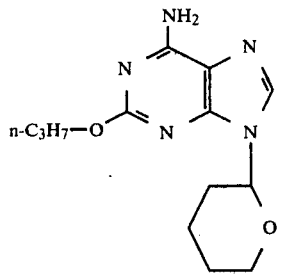

A solution of 2-chloro-9-(tetrahydropyran-2-yl)-9H-adenine (253 mg., 1 mmole) in 10 ml. of 1 N sodium n-propoxide in n-propanol is refluxed under a nitrogen atmosphere for a 1 hr. period. The reaction mixture is neutralized with acetic acid and evaporated to dryness in vacuo. Trituration of residual material with water affords 213 mg. of product which crystallized from ethyl acetate-n-hexane yields 147 mg. (57%) of analytically pure 2-n-propoxy-9-(tetrahydropyran-2-yl)-9H-adenine, m.p. 138.5–140° C. IR(KBr): 3500, 1630, 1605 cm$^{-1}$. UV: $\lambda_{max}^{MeOH}$ 268nm($\epsilon$12,600). NMR(CDCl$_3$): $\delta$1.03(3H,t,J=7.5 Hz), 1.4~2.3(8H,m), 3.4~4.2(2H,m), 4.2(2H,t,J=7.5 Hz), 5.4~5.7(1H,m), 5.81(2H,br,s), 7.71(1H,s).

Anal. Calcd. for $C_{13}H_{19}N_5O_2$: C, 56.30; H, 6.91; N, 25.25. Found: C, 56.05; H, 6.93; N, 25.26.

EXAMPLE 4

2-(2-Butoxy)-9-(tetrahydropyran-2-yl)-9H-adenine

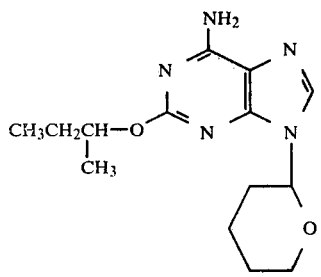

Reaction of 2-chloro-9-(tetrahydropyran-2-yl)-9H-adenine with 1 N sodium 2-butoxide in 2-butanol according to the procedure of Example 3 provides the title compound.

EXAMPLE 5

Pharmacological Evaluation

A. In Vitro Broncohdilator Activity

Tracheal chains of guinea pig were prepared by the method of A. Akcasu, Arch. Int. Pharmacodyn. Ther., 122, 201 (1959). The response to each test compound was recorded by the Magnus method and expressed as a percentage of the maximum response obtained with 0.1 mcg./ml. of isoproterenol prior to each experiment. Bronchodilator activity (in vitro) of aminophylline and test compounds of Examples 1–3 is expressed below as an EC$_{50}$ value (concentration in mcg./ml. which produces a relaxation which is 50% of the maximum response to 0.1 mcg./ml. of isoproterenol).

| In Vitro Test Results | |
|---|---|
| Compound of Example | EC$_{50}$ (mcg./ml.) |
| 1 | 0.45 |
| 2 | >3 |
| 3 | 0.17 |
| Aminophylline | 16.6 |

B. In Vivo Bronchodilator and Hypotensive Activity

The in vivo bronchodilator activity of aminophylline and test compounds was evaluated according to a modification of the method described by L. G. W. James, J. Pharm. Pharmac., 21, 379 (1969) by measuring decrease in intratracheal pressure (ITP) in the guinea pig. The trachea of anesthetized guinea pig was cannulated and the ITP recorded on a polygraph under artificial ventilation. Arterial blood pressure (ABP; reflecting hypotensive activity) was also measured during the experiment. Either intravenous or intraduodenal routes of administration are used. Results set forth below express the bronchodilator activity (ITP) as an ED$_{50}$ value (dose in mg./kg. resulting in a 50% decrease in intratracheal pressure) and the hypotensive activity (ABP) as an ED$_{20}$ value (dose in mg./kg which reduces arterial blood pressure by 20%). The ratio of hypotensive ED$_{20}$/bronchodilating ED$_{50}$ reflects an assessment of the separation of desirable bronchodilator activity from undesirable cardiovascular (hypotensive) effect in the compounds. Those compounds exhibiting the largest ABP/ITP ratios have the greatest separation of bronchodilator activity and hypotensive side effect.

| Compound of Examples | Intravenous Test Results (mg./kg) | | Ratio ABP/ITP |
|---|---|---|---|
| | ITP ED$_{50}$ | ABP ED$_{20}$ | |
| 1 | 0.23 | >1 | — |
| 2 | 2.2 | >1 | — |
| 3 | 0.26 | 1.9 | 7.3 |
| Aminophylline | 0.58 | 1.4 | 2.4 |

| Compound of Example | Intraduodenal Test Results (mg./kg.) | | Ratio ABP/ITP |
|---|---|---|---|
| | ITP ED$_{50}$ | ABP ED$_{20}$ | |
| 3 | 1.4 | 13.5 | 9.6 |
| Aminophylline | 5.9 | 9.5 | 1.6 |

EXAMPLE 6

Pharmaceutical Compositions

A. Tablets

The compounds of Formula I are compounded into tablets according to the following example:

| Materials | Amount |
|---|---|
| 2-n-Propoxy-9-(tetrahydropyran-2-yl)-9H-adenine | 20.0 g. |

-continued

| Materials | Amount |
| --- | --- |
| Magnesium stearate | 1.3 g. |
| Corn starch | 12.4 g. |
| Corn starch, pregelatinized | 1.3 g. |
| Lactose | 215.0 g. |

The foregoing materials are blended in a twin-shell blender and then granulated and pressed into tablets employing 250 mg. each. Each tablet contains about 20 mg. of active ingredient. The tablets may be scored and quartered so that unit doses of 5.0 mg. of active ingredient may be conveniently obtained.

B. Capsules

The purine derivatives of Formula I are compounded into capsules according to the following example:

| Materials | Amount |
| --- | --- |
| 2-n-Propoxy-9-(tetrahydropyran-2-yl)-9H-adenine | 50.0 g. |
| Lactose | 221.0 g. |
| Magnesium stearate | 4.0 g. |

The foregoing materials are blended in a twin-shell blender and No. 1 hard gelatin capsules filled with 275 mg. of the blended composition. Each capsule contains 50 mg. of active ingredient.

What is claimed is:

1. A compound having Formula I

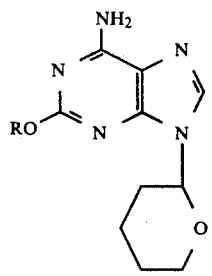

wherein R is lower alkoxy 1 to 4 carbon atoms inclusive or a pharmaceutically acceptable acid addition salt thereof.

2. The compound of claim 1 which is 2-methoxy-9-(tetrahydropyran-2-yl)-9H-adenine or a pharmaceutically acceptable acid addition salt thereof.

3. The compound of claim 1 which is 2-n-propoxy-9-(tetrahydropyran-2-yl)-9H-adenine or a pharmaceutically acceptable acid addition salt thereof.

4. A compound having Formula II

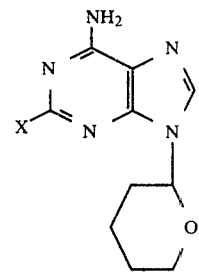

wherein X is halogen or a pharmaceutically acceptable salt thereof.

5. The compound of claim 4 which is 2-chloro-9-(tetrahydropyran-2-yl)-9H-adenine.

6. A bronchodilating process which comprises systemic administration to a mammal in need thereof an effective dose of from about 0.1 to 20 mg./kg. body weight of a compound of Formula I

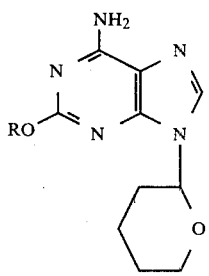

wherein R is lower alkyl of 1 to 4 carbon atoms inclusive or a pharmaceutically acceptable acid addition salt thereof.

7. The method as claimed in claim 6 wherein the active ingredient is 2-n-propoxy-9-(tetrahydropyran-2-yl)-9H-adenine.

* * * * *

UNITED STATES PATENT AND TRADEMARK OFFICE
CERTIFICATE OF CORRECTION

PATENT NO. : 4,241,063

DATED : December 23, 1980

INVENTOR(S) : Takayuki Naito, Susumu Nakagawa, Tetsuro Yamasaki, Taka-aki Okita, and Haruhiro Yamashita It is certified that error appears in the above—identified patent and that said Letters Patent is hereby corrected as shown below:

Column 9, line 45, change "alkoxy" to read -- alkyl --.

Signed and Sealed this

Fifth Day of May 1981

[SEAL]

Attest:

RENE D. TEGTMEYER

Attesting Officer     Acting Commissioner of Patents and Trademarks